United States Patent [19]

Julia et al.

[11] 4,343,952

[45] Aug. 10, 1982

[54] PROCESS FOR THE PREPARATION OF UNSATURATED SULPHONES

[75] Inventors: Marc Julia; Lucien Saussine, both of Paris, France

[73] Assignee: Agence Nationale de Valorisation de la Recherche (ANVAR), France

[21] Appl. No.: 195,003

[22] Filed: Oct. 8, 1980

[30] Foreign Application Priority Data

Oct. 11, 1979 [FR] France ............................. 79 25319

[51] Int. Cl.$^3$ ........................................... C07C 147/04
[52] U.S. Cl. .................................................... 568/28
[58] Field of Search .......................................... 568/28

[56] References Cited

U.S. PATENT DOCUMENTS

| | | | |
|---|---|---|---|
| 2,427,925 | 9/1947 | Samaniego et al. | 568/28 |
| 3,267,150 | 8/1966 | Moore et al. | 568/28 |
| 3,397,242 | 8/1968 | Klein | 568/28 |
| 3,848,000 | 11/1974 | Charbardes et al. | 568/28 |
| 3,850,991 | 11/1974 | Charbardes et al. | 568/28 |
| 3,876,707 | 4/1975 | Menet | 568/28 |

OTHER PUBLICATIONS

P. D. Magnus, *Tetrahedron*, vol. 33, pp. 2019-2045 (1977).

*Primary Examiner*—Mary C. Lee
*Attorney, Agent, or Firm*—Maky, Renner, Otto & Boisselle

[57] ABSTRACT

The present invention relates to a process for the preparation of unsaturated sulphones. It relates to a process in which unsaturated sulphones are prepared by sulphonation of the corresponding diene compound in the presence of a palladium catalyst, the sulphonating agent being a sulphinic acid or a sulphinate in the presence of an acid. The sulphones obtained are synthesis intermediates, particularly in the preparation of vitamins A and E.

14 Claims, No Drawings

PROCESS FOR THE PREPARATION OF UNSATURATED SULPHONES

FIELD OF THE INVENTION

This invention relates to a process for the preparation of unsaturated sulphones, in particular of allyl sulphones.

DESCRIPTION OF THE PRIOR ART

The usefulness of sulphones, in particular allyl sulphones, in synthesis as described in P. D. Magnus, Tetrahedron (Report), 1977, 33, 2019, especially as a synthesis intermediate in the preparation of important molecules such as terpenes and Vitamins A and E, has led to research into new methods of obtaining such sulphones.

It is known that such allyl sulphones can be prepared by the action of allyl alcohol in an acidic medium or of allyl halides on alkaline sulphinates. The allyl halides are often themselves obtained from conjugated dienes. This type of synthesis is employed, in particular, for the preparation of prenyl sulphone and geranyl sulphone, which are important intermediates for obtaining chrysanthemic acid, ionones and vitamins A and E respectively.

However, the preparation, stability and reactivity of allyl halides leave much to be desired and have numerous disadvantages from the practical point of view. Moreover, since the allyl halides themselves are prepared from the corresponding dienes, it was of interest to find a process permitting allyl sulphones to be prepared directly from dienes.

SUMMARY OF THE INVENTION

Thus, the present invention provides a process for the preparation of sulphones corresponding to formula I:

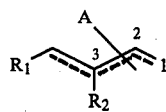

I in which the broken line represents a double bond in the 1, 2 or 3 position, A represents a substituted sulphonyl radical, in the α position relative to the double bond, and $R_1$ and $R_2$ each independently represent hydrogen, a substituted or unsubstituted alkyl, alkenyl or alkynyl radical, which comprises sulphonation, in the presence of a palladium catalyst, of a diene compound corresponding to the formula II:

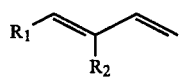

II in which $R_1$ and $R_2$ have the meanings given above, using at least one agent capable of introducing the substituted sulphonyl radical A selected from sulphinic acids or sulphinates in the presence of an acid, in a solvent, and separation of the sulphones and isomerisation of some of them, if necessary.

DETAILED DESCRIPTION OF THE INVENTION

Suitable substituted sulphonyl radicals A include, in particular, the alkyl sulphonyl, alkenyl sulphonyl radicals and, above all, the aryl sulphonyl radicals.

In the context of the present description, the term "alkyl radical" preferably refers to straight or branched alkyl radicals having from 1 to 30 carbon atoms and preferably from 1 to 10 carbon atoms such as the methyl, ethyl or propyl radicals.

Similarly, the alkenyl radicals are preferably straight or branched alkenyl radicals having from 2 to 30 carbon atoms and preferably from 2 to 10 carbon atoms, the said radicals being capable of having several double bonds which are preferably conjugated, such as the ethylenyl or 4-methyl-3-pentenyl radicals.

Finally, the alkynyl radicals are preferably straight or branched alkynyl radicals having from 2 to 30 carbon atoms and preferably from 2 to 10 carbon atoms.

These various radicals can also be substituted by one or more hydroxy or oxo functions and/or by cycloalkyl or cycloalkenyl radicals preferably containing 6 carbon atoms in the ring and which can themselves be substituted by one or more methyl radicals.

Suitable aryl sulphonyl radicals include, in particular, phenylsulphonyl radicals which are unsubstituted or substituted by one or more lower alkyl radicals, in particular methyl radicals, such as the toluene sulphonyl radicals.

Diene compounds corresponding to formula II which are of particular interest for carrying out the process to the present invention include butadiene, isoprene, myrcene and piperylene.

Compounds capable of introducing the aryl sulphonyl radical A include, in particular, the aryl sulphinic acids such as phenylsulphinic acid or p-toluene sulphinic acid, the mixture of aryl sulphinic acid and a corresponding sulphinate or the use of an aryl sulphinate in the presence of a weak acid such as acetic acid or formic acid. The alkaline aryl sulphinates are preferably used for convenience.

Suitable palladium catalysts include, in particular, the concurrent use of a palladium salt or complex such as a π-allylpalladium derivative and a phosphine, in particular the use of bis-π-allyl chloropalladium and triphenyl phosphine, but it is also possible to use other palladium complexes such as tetrakis-triphenyl-phosphine palladium (O) in the presence of a triphenyl phosphine.

The reaction is preferably carried out in an organic solvent such as tetrahydrofuran (THF).

As it is preferred to carry out the reaction in the liquid state and for the majority of the dienes used to be gases, the process is preferably carried out in a closed container at temperatures of between about 5° C. and about 100° C., preferably between 20° and 80° C. The reaction can be carried out in an inert atmosphere, for example, an argon atmosphere.

Although it is possible to use equimolar quantities of the diene and the agent for introducing the radical A, it is preferred to use an excess of diene which may be as much as 20/1 in moles.

The quantity of catalyst used is not a critical parameter and can vary within wide limits.

However, the molar ratio between the palladium derivative and the phosphine should generally be at least 1 and may be as much as 1/10 or higher.

After several tens of hours of reaction, a mixture of sulphones corresponding to formula I is generally obtained, generally containing the most highly substituted sulphone derivative as main product.

The various sulphones in the mixture can be separated by any known processes. In particular, it is possible to carry out recrystallisation in ethereal mixtures and/or separation by chromatography or mere distillation.

As primary sulphones are the particularly valuable sulphones, it is possible to isomerise the sulphones corresponding to formula Ia:

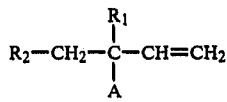

in order to prepare sulphones corresponding to formula Ib:

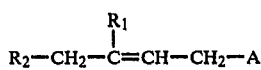

by the action of a sulphinate, for example, an alkaline sulphinate, preferably in the presence of an organic solvent such as THF and water at a temperature of between 5° C. and the reflux temperature of the mixture.

The sulphinate used is preferably the sulphinate corresponding to the radical A.

Under these conditions, the sulphones corresponding to formula Ib are obtained in a virtually quantitative yield, possibly in the form of a mixture of the E and Z isomers.

If desired, it is possible to isomerise the sulphones directly in the reaction mixture from the synthesis stage.

The various starting materials are known or can be prepared by known processes, some of which will be described more specifically in the following examples.

With regard to the various sulphones prepared, their uses in the synthesis of chemically important compounds are known or described in the general article mentioned above.

EXAMPLE 1

Preparation of 3-phenylsulphonyl butene-1 and 1-phenylsulphonyl butene-2

20 mg (0.1 m mole) of bis-π-allylchloropalladium prepared by the process of M. Sakakibara, Y. Takahashi, S. Sakai and Y. Ishii, Chem. Comm., (1969) 396, 82 mg (0.5 m mole) of sodium phenylsulphinate, 52 mg (0.2 m mole) of triphenylphosphine, 1.41 g (10 m moles) of sulphinic acid, 10 ml of THF and 3.5 ml (40 m moles) of butandiene are placed in a sealed tube and left for 65 hours at 20° C. After opening the tube, the solvent and the butadiene are evaporated, and the untreated product is washed with a saturated solution of sodium bicarbonate and extracted with ether.

After drying and evaporation of the ether, 2.0 g (9.5 m moles) (95%) of 3-phenylsulphonyl butene-1 and 1-phenylsulphonyl butene-2 sulphone mixture are obtained in the respective proportion of 80 to 20 (by VPC quantitative analysis and comparison of the NMR spectrum of the untreated product with that of a mixture of the two genuine sulphones).

EXAMPLE 2

Preparation of 3-p-toluenesulphonyl butene-1 and 1-p-toluenesulphonyl-1 butene-2

60 mg (0.3 m moles) of bis-π-allylchloropalladium, 266 mg (1.5 m moles) of sodium p-toluenesulphinate, 396 mg (1.5 m moles) of triphenylphosphine and 4.7 g (30 m moles) of p-toluenesulphinic acid and then 15 ml of anhydrous THF are placed in a sealed tube. After cooling the mixture to −80° C., 5 ml (40 m moles) of liquid butadiene are added.

After 18 hours at 30° C., 1.75 g of untreated product containing palladium, triphenylphosphine and sulphones are collected after evaporation of the solvents, washing with a saturated solution of sodium bicarbonate and extraction with ether.

Results obtained by CPV and NMR:

| 3-p-toluenesulphonyl butene-1 | 30% |
|---|---|
| 1-p-toluenesulphonyl butene-2 (E) | 12% |

Pure 3-p-toluenesulphonyl butene-1 is separated by crystallisation in ether: 0.82 g (15%, based on the starting sulphinic acid)
M.P. = 70° C. (Ether)
IR: cm$^{-1}$ 1120, 1280
NMR 80 MHz: 1.43 (d,7,3H); 1.46 (s,3H); 3.7 (m,1H); 5 to 6.2 (m,3H); centred at 7.6 (q,AA'BB',4H).
Mass: 210.

3-p-toluenesulphonyl butene-1 and 1-p-toluenesulphonyl butene-2 described by P. Bickart, F. W. Carson, J. Jacobus, E. G. Miller and K. Mislow, J. Amer. Chem. Soc., (1968) 4869.

EXAMPLE 3

Isomerisation of 3-p-toluenesulphonyl butene-1

210 mg (1 m mole) of 3-p-toluenesulphonyl butene-1, 178 mg (1 m mole) of sodium p-toluenesulphinate, 9 mg (0.5 m mole) of water and 2 ml of THF are placed in a flask. The mixture is brought to 60° C. and the evolution is followed by VPC:
70% of primary sulphone and 30% of secondary sulphone are present after 30 minutes.
95% of primary sulphone and 5% of secondary sulphone are present after 2 hours or 7 hours.

50 ml of ether are added after 7 hours and the p-toluenesulphinate is filtered. After evaporation of the solvents, 202 mg (96%) of the following sulphones are collected.

| 1-p-toluenesulphonyl butene-2 (E) | 64% |
|---|---|
| 1-p-toluenesulphonyl butene-2 (Z) | 27% |
| 3-p-toluenesulphonyl butene-1 | 5% |

These proportions are established by NMR according to the data given by P. Bickart, F. W. Carson, J. Jacobus, E. G. Miller and K. Mislow J. Amer. Chem. Soc. (1968) 4869, and the spectrum of the genuine product.

EXAMPLE 4

Preparation of 2-phenylsulphonyl-2-methyl butene-3

20 mg of bis-π-allylchloropalladium (0.1 m mole of Pd), 82 mg (0.5 m mole) of sodium phenylsulphinate, 52 mg (0.2 m mole) of triphenylphosphine, 1.41 g (10 m moles) of phenylsulphinic acid then 20 ml of tetrahydrofuran and 15 ml (≃150 m moles) of isoprene are placed in a tube which is then sealed under vacuum. The solvent is evaporated after 72 hours at 20° C. and 2.25 g of unreacted product are obtained.

VPC anaylsis of the untreated product demonstrates that a single product is present (SE 30; 2.5%; 3 m; Anachrom SD 70–80 mesh; 190° C.).

Chromatography over silica (Merck (60) 70 to 230 mesh; ASTM) with methylene chloride as eluant gives 2 g (96%) of pure sulphone.

Mass: 210, 143, 77, 69.
Analysis: $C_{11}H_{14}O_2S$.
NMR 80 MHz: 1.43 (s, 6H) vinyl multiplet: (4.93, 5.22, 5.37 (2H)), (5.83, 6.01, 6.12, 6.3 (1H)), 7.45 to 8.05 (5H).
IR: $cm^{-1}$ 1155, 1290.

EXAMPLE 5

Preparation of 2-p-toluenesulphonyl-2-methyl butene-3

40 mg (0.2 m mole of Pd) of bis-π-allylchloropalladium, 89 mg (0.5 m mole) of sodium p-toluenesulphinate, 52 mg (0.2 m mole) of triphenyl phosphine, 1.56 g (10 m moles) of p-toluenesulphinic acid then 20 ml of tetrahydrofuran and 2 ml (20 m moles) of isoprene are placed in a flask previously placed under argon. The mixture is left for 18 hours at 45° C. under argon and, after evaporation of the solvent and the isoprene, 2.3 g of untreated product are isolated.

VPC analysis indicates the presence of sulphones in the following proportions:

| 2-p-toluenesulphonyl-2-methyl butene-3 | 93% |
|---|---|
| 1-p-toluenesulphonyl-3-methyl butene-2 | 5% |
| p-tolylallylsulphone | 2% |

2.05 g (92%) of 2-p-toluenesulphonyl-2-methyl butene-3 sulphone are isolated by chromatography over silica (Merck (60), 70 to 230 mesh, AST) with the mixture (methylene chloride 45/cyclohexane 45/ethyl acetate 5) and then recrystallised in an ether 50/pentane 50 mixture.

M.P.: 51°–52° C.
Analysis: $C_{12}H_{16}O_2S$.
Mass: 224.
NMR 80 MHz: 1.375 (s,6H), 2.38 (s,3H) 4.90 to 5.40 (m,2H), 6.0 (m, J=10, J'=17,1H), 7.30 (d,2H) 7.70 (d,2H)
NMR 13C: 20.8 (2CH₃), 21.6 (CH₃), 64.5 (C), 118.4 (CH₂), 128.7 (2CH) 130.2 (2CH), 132.0 (C), 136.4 (CH) 144.1 (C).
VPC: 190° C., 7 mn.

EXAMPLE 6

Preparation of 2-p-toluenesulphonyl-2-methyl butene-3

40 mg (0.2 m mole of Pd) of bis-π-allylchloropalladium, 1.78 g (10 m moles) of sodium p-toluenesulphinate, 260 mg (1 m mole) of triphenyl phosphine, 10 ml of THF, 0.70 g (10 m moles) of acetic acid and 2 ml (20 m moles) of isoprene are placed in a flask under argon. The mixture is left for 18 hours at 25° C. under argon, the solvent and isoprene are then evaporated, and the untreated product is washed with a saturated solution of sodium bicarbonate and extracted with ether. After drying over magnesium sulphate and evaporation of the ether, 1.255 g of untreated product (41% of sulphones obtained) also containing some triphenyl phosphine and coloured palladium complexes (brownish red) are obtained. The product is dissolved in 20 ml of cyclohexane, and an air stream (100 ml/mn) is passed over it for 30 minutes. The product is then filtered over 10 g of silica for plates (Kieseigel 60 PF 254 Merck) and the sulphones are eluted from the silica by 50 ml of ether, yielding 0.820 g (36%) of sulphones after evaporation of the solvents.

The respective proportions of the sulphones are obtained by VPC:

| 2-p-toluenesulphonyl-2-methyl butene-3 | 92% |
|---|---|
| 1-p-tolysulphonyl-3-methyl butene-2 | 6% |
| allyl p-tolysulphone | 2% |

After recrystallisation in the pentane/ether mixture, 0.620 g (28%) of 2-p-toluenesulphonyl-2-methyl butene-3 sulphone is obtained which is similar in VPC, melting point and NMR to a genuine sample manufactured by the method of D. Savoia, C. Trombini and A. Umani-Ronchi, J.C.S. Parkin I, (1977) 123.

EXAMPLE 7

Isomerisation of 2-p-toluenesulphonyl-2-methyl butene-3

2-phenylsulphonyl-2-methyl butene-3 sulphone (224 mg, 1 m mole) is heated to 60° C. in tetrahydrofuran (2 ml) with sodium p-toluenesulphinate (178 mg, 1 m mole) in a suspension and water (9 mg, 0.5 m mole).

The appearance of the 1-p-tolylsulphonyl-3-methyl butene-2 sulphone is followed by VPC (SE 30, 2.5%, 3 m over Anachrom SD 70–80 mesh, 190° C. (10 mn). 50% of it are formed after 2.5 hours and 98% after 8.5 hours. The THF is then evaporated and the solids are washed with ether. 0.220 mg (98%) of 1-p-tolysulphonyl-3-methyl butene-2 sulphone are isolated by evaporation of the ether. NMR demonstrates that 1-p-tolylsulphonyl-3-methyl butene-2 is present (spectrum similar to that of the authentic 1-p-tolylsulphonyl-3-methyl butene-2 and to that described by F. G. Bordwell and T. Mecca, J. Amer. Chem. Soc., (1972) 5829 nd F. G. Bordwell and R. J. Kern, J. Amer. Chem. Soc., (1955) 1141), as well as VPC and the melting point, M.P.=80°–81° C.

EXAMPLE 8

Preparation of 3-p-toluenesulphonyl-3,7-dimethyl octadiene-1,6 (p-tolyllinalylsulphone)

520 mg (3.5 m moles) of sodium p-toluenesulphinate, 9.2 g (59 m moles) of p-toluenesulphinic acid, 300 mg (1.9 m moles of Pd) of bis-π-allylchloropalladium, 1.9 g (7.5 m moles) of triphenyl phosphine (90 m moles), 15 ml of myrcene and 60 ml of anhydrous THF are placed in a flask under argon and then heated for 18 hours at 60° C. The solvent is evaporated, the untreated product is washed with a saturated solution of sodium bicarbonate and the product is extracted with methylene chloride. Chromatography on a silica column (Merck (60), 70 to 230 mesh) eluted with a mixture of methylene chloride 48/cyclohexane 48/ethyl acetate/4 yields (87%) 15 g of 3-p-toluenesulphonyl-3,7-dimethyl octadiene-1,6 (p-tolyllinalylsulphone) and (5.8%) 1 g of 1-p-toluenesulphonyl-3,7-dimethyl octadiene-2,6 (E).

3-p-toluenesulphonyl-3,7-dimethyl octadiene-1,6 (p-tolyllinalylsulphone):
M.P.=70° C. (Pentane/ether)

VPC: 210° C., 15 mn
NMR 250 MHz: 1.38 (s,3H), 1.57 (s,3H), 1.67 (s,3H) 1.92 (m,4H), 2.44 (s,3H), 5.1 (m,1H), 5.1 (d,17.5,1H), 5.36 (d,10.5,1H), 5.9 to 6 (c,10.5, 17.5,1H), 7.30 (m,2H), 7.68 (m,2H).
Analysis: $C_{17}H_{24}O_2S$ Mass=293, 292, 157, 155 ...
NMR$^{13}$C: 16.3 ($CH_3$), 17.6 ($CH_3$), 21.6 ($CH_3$), 22.5 ($CH_2$), 25.6 ($CH_3$), 32.9 ($CH_2$), 68.0 (C), 120.0 ($CH_2$), 122.8 (CH), 128.7 (2CH), 130.3 (2CH), 132 (2C), 135.0 (CH), 144.0 (C).
1-p-toluenesulphonyl-3,7-dimethyl octadiene-2,6 (geranyl and neryl sulphones by isomerisation of linalulsulphone): identified by an authentic sample.

EXAMPLE 9

Preparation of 3-p-toluenesulphonyl-3,7-dimethyl octadiene-1,6 (p-tolyllinalylsulphone)

1.78 g (10 m moles) of sodium p-toluenesulphinate, 260 mg (1 m mole) of triphenyl phosphine, 40 mg (2 m moles of Pd) of bis-$\pi$-allylchloropalladium, 0.60 g of acetic acid (10 m moles), 1.7 ml (10 m moles) of myrcene and 10 ml of THF are placed in a flask under argon. After 18 hours of stirring at 25° C., the solvent is evaporated, and the untreated product is washed with a saturated solution of sodium bicarbonate and extracted with ether. After drying over magnesium sulphate, evaporation of the ether and distillation of the remaining myrcene (ball tube under 11 mm Hg) (0.5 g=35%), the untreated product contains triphenyl phosphine and palladium as well as a mixture of sulphones obtained in the following yields:

| | |
|---|---|
| 3-p-toluenesulphonyl-3,7-dimethyl octadiene-1,6 (p-tolyllinalysulphone) | 35% |
| 1-p-toluenesulphonyl-3,7-dimethyl octadiene-2,6 (E) | 6.7% |
| 1-p-toluenesulphonyl-3,7-dimethyl octadiene-2,6 (Z) calculated by VPC. | 1.3% |

These sulphones were compared to the data given in the literature and to those obtained previously in NMR proton, NMR$^{13}$C, VPC and melting points.

EXAMPLE 10

Preparation of 1-p-toluenesulphonyl-3,7-dimethyl octadiene-2,6 (geranyl and neryl sulphones by isomerisation of linalyl sulphone)

0.292 g (1 m mole) of 3-p-toluenesulphonyl-3,7-dimethyl octadiene-1,6 (p-tolyllinalysulphone), 0.178 g (1 m mole) of sodium p-toluenesulphinate, 2 ml of THF and 9 mg (0.5 m mole) of water are placed in a flask. The mixture is heated at 60° C. for 40 hours, 50 ml of ether are then added and the mixture is filtered. After evaporation of the filtrate, 0.290 g (99%) of 1-p-toluenesulphonyl-3,7-dimethyl octadiene-2,6 sulphones are obtained in proportions of Z/E=20/80. 58 mg (20%) of 1-p-toluenesulphonyl-3,7-dimethyl octadiene-2,6 (Z) and 230 mg (79%) of 1-p-toluenesulphonyl-3,7-dimethyl octadiene-2,6 (E) are collected quantitatively by silica plate chromatography (Merck) eluted with a mixture of $CH_2Cl_2$ 50/cyclohexane 50/ethyl acetate 5.
1-p-toluenesulphonyl-3,7-dimethyl octadiene-2,6 (Z): oil.
analysis: $C_{17}H_{24}O_2S$.
VPC: 210° C., 16 mn.
Mass: 292.
NMR 250 MHz: 1.54 (s,3H), 1.66 (s,3H), 1.74 (s,3H), massive 1.75 to 2 (m,4H), 2.44 (s,3H), 3.78 (d,2H), 4.95 (t, 7,1H), 5.20 (t, 8,1H), 7.32 (m,2H), 7.74 (m,2H),
NMR$^{13}$C: 17.8 ($CH_3$), 21.7 ($CH_3$), 23.7 ($CH_3$), 25.7 ($CH_3$), 26.2 ($CH_2$), 32.0 ($CH_2$), 56.1 ($CH_2$), 110.9 (CH), 123.2 (CH), 128.2 (2CH), 129.4 (2CH), 132.0 (C), 136.0 (C), 144.1 (C), 145.5 (C)
1-p-toluenesulphonyl-3,7-dimethyl octadiene-2,6 (E): is recrystallised in pentane/ether.
M.P.=44° C.
VPC: 210° C., 19 mn.
Mass: 292
NMR 80 MHz: 1.36 (s, 3H), 1.61 (s, 3H), 1.70 (s, 3H), 1.95 to 2.15 (m, 4H), 2.45 (s, 3H), 3.81 (d, 8, 2H), 4.85 to 5.50 (m, 2H), 7.38 (m, 2H), 7.83 (m, 2H).
NMR$^{13}$C: 16.3 ($CH_3$), 17.8 ($CH_3$), 21.7 ($CH_3$), 25.7 ($CH_3$), 26.3 ($CH_2$), 39.7 ($CH_2$), 56.2 ($CH_2$), 110.3 (CH), 123.3 (CH), 128.3 (2CH), 129.2 (2CH), 131.7 (C), 135.7 (C), 144.1 (C), 145.7 (C).
Allocation of the structures (E) and (Z) for 1-p-toluenesulphonyl-3,7-dimethyl octadiene-2,6 according to L. Grombie, R. V. M. Campbell, D. A. R. Finlley, R. W. King, G. Pattenden and D. A. Whitting, J.C.S. Perkin I, (1975) pp 897 to 915, giving the proton and $^{13}$C NMR of geranyl and neryl phenylsulphones, in the same manner as M. Julia and D. Uguen, Bull Soc. Chim. France (1976) 513.

EXAMPLE 11

Preparation of 2-p-toluenesulphonyl pentene-3, 1-p-toluenesulphonyl pentene-2 and 3-p-toluenesulphonyl pentene-1

40 mg (0.2 m mole of Pd) of bis-$\pi$-allylchloropalladium, (0.5 m mole) 89 mg of sodium p-toluenesulphinate, 52 mg (0.2 m mole) of triphenyl phosphine, 1.56 g (10 m moles) of p-toluenesulphinic acid, 2 ml of piperylene (20 m moles) and 20 ml of THF are placed in a flask under argon. The mixture is heated for 18 hours at 40° C. The solvent is evaporated, and the untreated product is then washed with a saturated solution of sodium bicarbonate and extracted with methylene chloride. 2.30 g of a mixture of 2-p-toluenesulphonyl pentene-3, 1-p-toluenesulphonyl pentene-2 and 3-p-toluensulphonyl pentene-1 sulphones are collected with triphenyl phosphine and palladium. The following isomeric sulphones in the untreated product:

| | |
|---|---|
| 2-p-toluenesulphonyl pentene-3 (E) | (70%) |
| 1-p-toluenesulphonyl pentene-2 (E) | (10%) |
| 3-p-toluenesulphonyl pentene-1 | (15%) |
| p-tolylallylsulphone | (2%) | are determined by VPC and by NMR 250 MHz in comparison with authentic samples.

We claim:

1. A process for the preparation of sulphones or of a mixture of sulphones corresponding to Formula I:

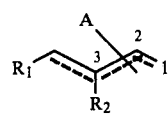

in which the broken line represents a single double bond in the 1, 2 or 3 position, A represents a substituted sulphonyl radical placed in the alpha position relative to the double bond, the substituents on said sulphonyl radical being selected from the group consisting of alkyl groups of 1 to 30 carbon atoms, alkenyl or alkynyl groups of 2 to 30 carbon atoms, or a phenyl group, said alkynyl, alkenyl, alkynl or phenyl groups being unsubstituted or substituted with one or more hydroxy, oxo, methyl, or cycloalkyl or cycloalkenyl groups containing 6 carbon atoms in the ring which can be unsubstituted or substituted with one or more methyl groups and $R_1$ and $R_2$ represent hydrogen, a substituted or unsubstituted alkyl radical of 1 to 30 carbon atoms or, alkenyl or alkynyl radical of 2 to 30 carbon atoms, the substituents on said alkyl, alkenyl or alkynl radicals being one or more hydroxy or oxo functions or one or more cycloalkyl or cycloalkenyl groups containing 6 carbon atoms in the ring which is unsubstituted or substituted with one or more methyl groups, which comprises sulphonating, in the presence of a palladium catalyst and in a solvent, a diene compound corresponding to Formula II:

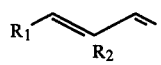 II in which $R_1$ and $R_2$ have the meanings given above, using at least one agent capable of introducing the substituted sulphonyl radical A selected from sulphinic acids and sulphinates in the presence of a weak acid, and separating the sulphones.

2. A process according to claim 1, wherein the radical A is an arylsulphonyl radical.

3. A process according to claim 2, wherein the agent for instroducing the arylsulphonyl radical A is a mixture of an arylsulphinic acid and a corresponding arylsulphinate.

4. A process according to claim 2, wherein the agent for introducing the arylsulphonyl radical A is an arylsulphinic acid.

5. A process according to claim 2, wherein the agent for introducing the arylsulphonyl radical A is an arylsulphinate in the presence of acetic or formic acid.

6. A process according to claim 1, wherein the palladium catalyst is constituted of a palladium salt or complex and is used in the presence of a phosphine.

7. A process according to claim 6, wherein the palladium complex is selected from a $\pi$-allyl palladium derivative and palladium tetrakis-triphenylphosphine.

8. A process according to claim 6, wherein the phosphine is triphenyl phosphine.

9. A process according to claim 7, wherein the phosphine is triphenyl phosphine.

10. A process according to claim 1, wherein the solvent is tetrahydrofuran.

11. A process according to claim 1, wherein the diene compound corresponding to formula II is selected from butadiene, piperylene, myrcene and isoprene.

12. A process according to claim 1 with the step of isomerizing some of said sulphones, sulphones corresponding to the Formula Ia:

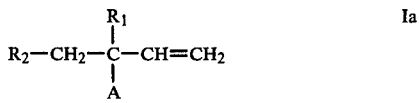 Ia being isomerized into a sulphone corresponding to the Formula Ib:

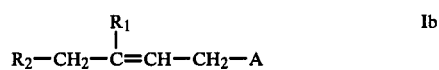 Ib by the action of a sulphinate in the presence of water and an organic solvent.

13. A process according to claim 12, wherein the sulphinate used for isomerisation is a sulphinate corresponding to the radical A of the sulphones Ia and Ib, and wherein the organic solvent is tetrahydrofuran.

14. A process according to claim 12 or 13 wherein said sulphones are isomerized directly in the reaction mixture from the synthesis stage.

* * * * *